United States Patent
Choi et al.

(10) Patent No.: US 7,132,112 B2
(45) Date of Patent: *Nov. 7, 2006

(54) TRANSNASAL ANTICONVULSIVE COMPOSITIONS AND MODULATED PROCESS

(75) Inventors: Yong Moon Choi, Towaco, NJ (US); Lianli Li, Fresh Meadows, NY (US); Kwon H. Kim, Bridgewater, NJ (US)

(73) Assignee: SK Corporation (KR)

(*) Notice: Subject to any disclaimer, the term of this patent is extended or adjusted under 35 U.S.C. 154(b) by 0 days.

This patent is subject to a terminal disclaimer.

(21) Appl. No.: 10/634,689

(22) Filed: Aug. 5, 2003

(65) Prior Publication Data

US 2004/0028617 A1  Feb. 12, 2004

Related U.S. Application Data

(63) Continuation of application No. 09/624,305, filed on Jul. 24, 2000, now Pat. No. 6,627,211.

(60) Provisional application No. 60/145,590, filed on Jul. 26, 1999.

(51) Int. Cl.
  *A61F 13/00* (2006.01)
  *A61L 9/04* (2006.01)

(52) U.S. Cl. .................... 424/434; 424/45

(58) Field of Classification Search ........ 424/434, 424/45; 514/178, 975
  See application file for complete search history.

(56) References Cited

U.S. PATENT DOCUMENTS 4,863,720 A   9/1989  Burghart et al. ........... 424/45
4,950,664 A   8/1990  Goldberg ................... 514/219
5,428,006 A   6/1995  Bechgaard et al. ......... 514/3
6,627,211 B1* 9/2003 Choi et al. ................ 424/434

FOREIGN PATENT DOCUMENTS

WO   WO 91/16929 A   11/1991

OTHER PUBLICATIONS

Supplementary European Search Report, Nov. 29, 2004.

* cited by examiner

*Primary Examiner*—Lakshmi Channavajjala
(74) *Attorney, Agent, or Firm*—Gibbons, Del Deo, Dolan, Griffinger and Vecchione

(57) ABSTRACT

A novel method of vehicle modulated administration of an anticonvulsive agent to the mucous membranes of humans and animals is disclosed. The vehicle system is an aqueous pharmaceutical carrier comprising an aliphatic alcohol (10–80%) or a glycol (10–80%), and their combinations with a biological surfactant such as a bile salt or a lecithin. The pharmaceutical composition provides a means to control and promote the rate and extent of transmucosal permeation and absorption of the medicaments via a single and multiple administration. Nasal administration of the pharmaceutical preparation produces a high plasma concentration of the anticonvulsant nearly as fast as intravenous administration. Such compositions are particularly suitable for a prompt and timely medication of patients in the acute and/or emergency treatment of status epilepticus and other fever-induced seizures.

3 Claims, 9 Drawing Sheets

Rabbit Nasal Mucosa

TRANSNASAL ANTICONVULSIVE COMPOSITIONS AND MODULATED PROCESS

RELATED APPLICATIONS

This application is a continuation of patent application Ser. No. 09/624,305, filed Jul. 24, 2000, now U.S. Pat. No. 6,627,211, which, in turn is a continuation of Provisional Patent Application No. 60\145,590, filed Jul. 26, 1999.

FIELD OF THE INVENTION

The present invention is directed to pharmaceutical compositions for transmucosal delivery of biologically active agents. More particularly, this invention relates to a novel method for controlling and promoting the rate and extent of transmucosal permeation and absorption of an anticonvulsive agent by coadministration of the medicament with a pharmaceutically acceptable co-solvent system comprising an aliphatic alcohol, a glycol, and water, and their combinations with a biological surfactant such as a bile salt or a lecithin. Even more particularly, this invention relates to the pharmaceutical compositions to provide a patient-acceptable transnasal anticonvulsive delivery system, which may be useful for the emergency management of status epilepticus and fever seizures in a prompt and convenient manner of administration.

BACKGROUND OF THE INVENTION

Status epilepticus is a neurological emergency in which mortality ranges from 3–35%. The major goal of treatment is rapid management of pathological seizure activity; the longer that the episode of status epilepticus is untreated, the more difficult it is to control and the greater the risk of permanent brain damage. Thus, critical to the management of the patient is a clear plan, involving prompt treatment with effective drugs in adequate doses having a proper pharmaceutical formulation as well as attention to hypoventilation and hypotension.

Currently several drug regimens have been proven to be applicable in treating status epilepticus. Diazepam and lorazepam are the most widely used benzodiazepines for this purpose. Intravenous administration of anticonvulsants is the most rapid way to suppress epileptic convulsions. However, other routes of administration may be highly desirable when intravenous administration is inconvenient and delaying, for instance, because of technical difficulties such as requirements for sterile equipment and skilled personnel, and because of the possible development of thrombophlebitis. In addition, intravenous medication is often associated with hypotension, cardiac dysrhythmia or central nervous system depression. In this regard Moolenaar [Moolenaar et al., *Int. J. Pharm.*, 5: 127–137 (1986)] attempted to administer diazepam in humans via several other routes such as intramuscular injection, oral tablet and rectal solution. Only the rectal administration was found to provide a fairly rapid absorption and thus, it might be looked upon as an alternative route to IV injection. However, the rectal route is a very inconvenient way of drug administration particularly in emergency treatment. In U.S. Pat. No. 4,863,720 of Burghardt, a sublingual sprayable pharmaceutical preparation is disclosed, in which the active drug can be a benzodiazepine, optimally comprising polyethylene glycol (PEG) and requiring ethanol, di- and/or triglyceride of fatty acids and a pharmaceutically acceptable propellant gas.

More recently, it appears that the mucosal membrane of the nose offers a practical route of administration for therapeutic effect of many medicinal substances. Intranasal administration has the advantages that drugs may be administered readily and simply to achieve a systemic or localized effect, as required. However, the major problem associated with intranasal drug administration is the fact that most drug molecules diffuse poorly and slowly through the nasal mucosal membrane and thus the desired levels of the therapeutic agent cannot be achieved by means of simple transnasal administration. An additional constraint concerning nasal administration is that a small administration volume is needed; it is not generally possible to administer more than approximately 150 μl per nostril; above this, the formulation will be drained out into the pharynx and swallowed. Therefore, a great need exists for solvent vehicles, in which the solubility of the drug is high and which, on the other hand, are non-irritating to the nasal mucosa. The intranasal absorption of drugs can be increased by coadministering a chemical adjuvant or permeation enhancers. For example, Lau and Slattery [Lau et al., *Int. J. Pharm.*, 54: 171–174 (1989)] attempted to administer a benzodiazepine such as diazepam and lorazepam by dissolving these medicaments in a variety of solvents; triacetin, dimethylsulfoxide, PEG 400, Cremophor EL, Lipal-9-LA, isopropyl adipate and Azone. While many of the solvents dissolved diazepam and lorazepam in the desired concentrations, they were too irritatable to be used, when administered to the nose. Cremophor EL was found to be the least irritating for nasal mucosal tissue, but the nasal absorption in the use of this vehicle in humans was rather slow ($T_{max} \cong 1.4$ hours) and the peak concentration was low relative to that observed after IV administration. In U.S. Pat. No. 4,950,664 of Rugby described the nasal administration of a benzodiazepine hypnotic in a pharmaceutically acceptable nasal carrier. The carrier may be an aqueous saline solution, an alcohol, a glycol, a glycol ether or mixtures thereof. The results of pharmacokinetic studies in dogs showed that the time to maximum plasma concentration for triazolam was achieved at 18 minutes after the nasal administration, while an effective treatment within 5 minutes is considered to be an attractive goal. Bechgaard and Hjortkjer [Bechgaard et al., *J. Pharm. Pharmacol.*, 49: 747–750 (1997)] described the use of pure organic solvents such as glycofurol and tetraethyleneglycol, and their combinations as carriers for nasal delivery of diazepam. The absolute bioavailability, measured during the first 30 minutes, after the nasal administration, was 49–62% for the most promising carrier systems examined. In PCT WO 95/31217, Dumex described the use of a pharmaceutical emulsion preparation based on tocopherol and its derivatives for intranasal administration of biologically active compounds including benzodiazepines.

SUMMARY OF THE INVENTION

The present invention is a novel method of vehicle modulated administration of an anticonvulsive agent to the mucous membranes of humans and animals. The vehicle system is an aqueous pharmaceutical carrier comprising an aliphatic alcohol or a glycol and their combinations with a biological surfactant such as a bile salt or a lecithin.

An objective of the present invention is to provide a pharmaceutically acceptable carrier system which is capable of enhancing the transmucosal permeation and absorption of an anticonvulsive agent. The ingredients used in the pharmaceutical composition are preferably those of GRAS materials (generally recognized as safe), so there are no major toxicity issues of concern. Another objective of the present invention is to provide a method of controlling the transmucosal delivery of an anticonvulsant at an appropriately adjusted rate so as to achieve an optimum therapeutic effect, while avoiding or reducing adverse side effects. Such compositions are particularly suitable for intranasal administration of the medicaments in the acute treatment of status epilepticus and fever seizures.

DETAILED DESCRIPTION OF THE INVENTION

Figure 1:
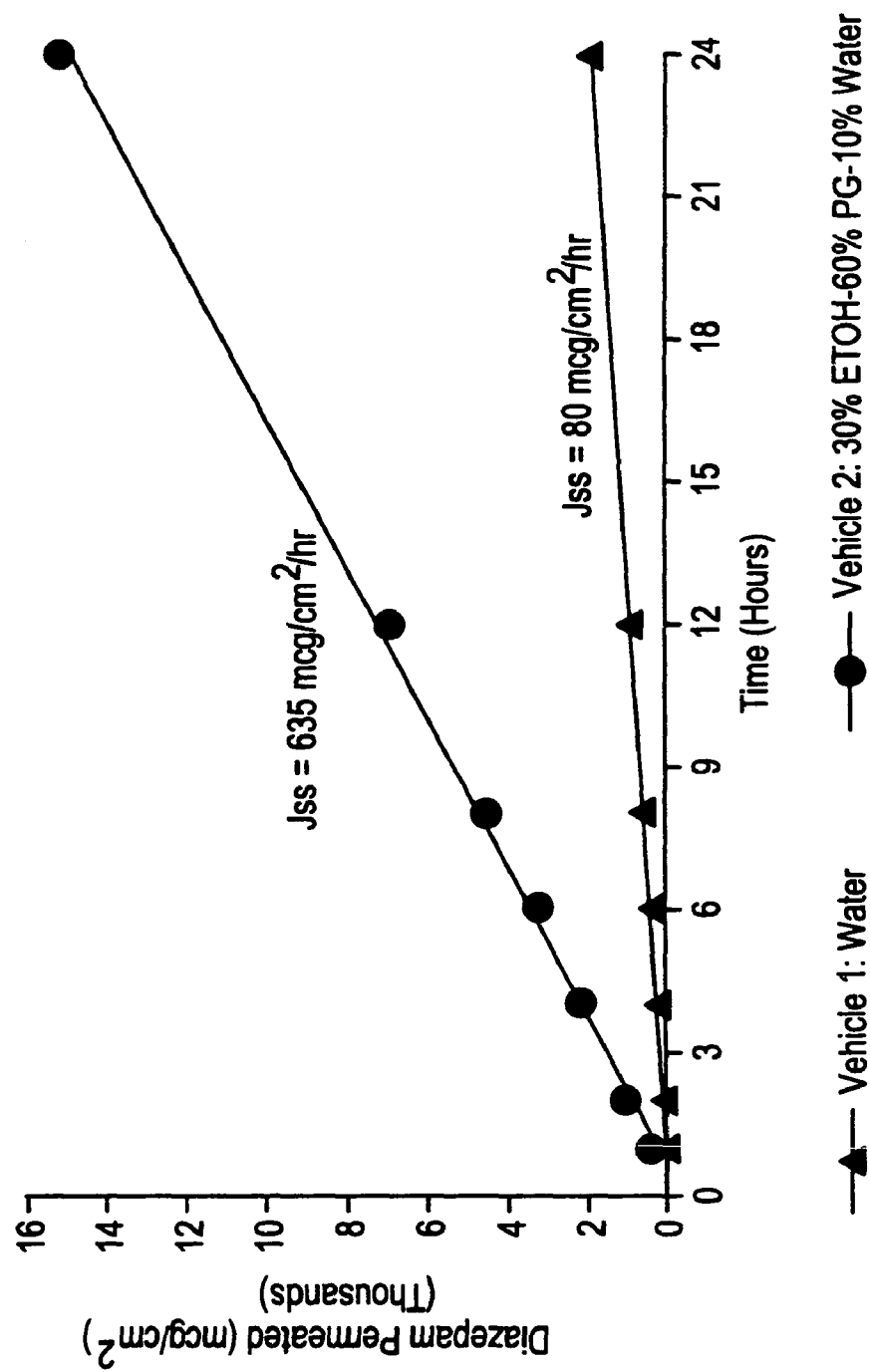
FIG. 1 is a graph showing the effect of a vehicle on the in vitro transnasal permeation of diazepam preparations of the invention.

In accordance with the present invention, a certain aqueous co-solvent system comprising one aliphatic alcohol, one glycol and a biological surfactant provides a rate-controlled and enhanced transnasal delivery of an anticonvulsive agent. The alcohol of the present invention is selected from $C_1$ to $C_5$ aliphatic alcohols; a glycol is selected from propylene glycol, polyethylene glycol (PEG) 200, PEG 300 and PEG 400, and PEG 600; and a biological surfactant is selected from bile salts such as sodium cholate, sodium deoxycholate, sodium taurocholate, sodium glycocholate, and sodium ursodeoxycholate or a lecithin such as lysophosphotidylcholine, dipalmitoylphosphotidylcholin, distearoylphosphotidylcholin, dipalmitoylphosphotidyl-ethanolamine, and dipalmitoylphosphotidylglycerol. The above-described compositions can be used for medicinal preparations comprising anticonvulsive agents applicable to the mucosal membranes of humans and animals. More specifically, these compositions are ones, which comprise a benzodiazepine such as diazepam, clonazepam, and lorazepam, and a monocarbamate based new anticonvulsive compound, (S)-2-carbamoyloxyl-1-o-chlorophenylethanol represented by the following formula:

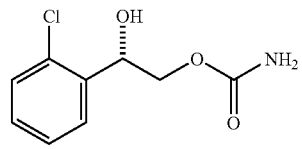

adapted for intranasal administration in a solution, suspension, gel or other useful nasal formulation. These nasal compositions may be employed for any of the known therapeutic purposes for which such anticonvulsants are known including phenytoins (phenytoin, mephenytoin and ethotoin), barbiturates (phenobarbital, mephobarbital, and primidone), iminostilbenes (carbamazepine), succinimides (ethosuximide), valproic acid, oxazolidinediones (trimethadione) and other antiseizure agents (gabapentin, lamotrigine, acetazolamide, felbamate, and γ-vinyl GABA). The utilization of an intranasal formulation of the anticonvulsant greatly facilitates administration. As compared with parenteral administration, for example, a simple sprayer, dropper or nebulizer will suffice for prompt and convenient delivery of the medicaments, in particular, for the emergency treatment of acute convulsive attack phenomena of epilepsy. From a clinical point of view, intranasal administration often provides an improved duration of anticonvulsive effect. By the present invention, the therapeutic effect, in terms of onset, intensity, and duration, can be more efficiently and accurately controlled by varying the proportion of aliphatic alcohol and glycol in the vehicle and by a single-dose and/or multiple-dose administration of the preparation of the invention. Although this invention has been described with respect to an anticonvulsant as a model compound, it is understood that this invention is also applicable to the other biologically active agents that are applicable to the mucosal membranes of humans and animals.

The invention is further illustrated by the following examples, which are illustrative of a specific mode of practicing the invention and is not intended as limiting the scope of the appended claims.

EXAMPLE 1

In Vitro Nasal Membrane Permeation Studies

The nasal mucous membrane used in these in vitro experiments was obtained from New Zealand White rabbits (2.5–3.0 kg). Rabbits were sacrificed by IV injection of phenobarbital. The nasal septum was carefully removed from a bone block using surgical scissors and a bone-cutting saw. Two pieces of nasal mucous membranes were then carefully stripped from the nasal septum without touching the center of the membrane surface and rinsed with normal saline solution. The mucosal membrane was mounted between two half-cells of a glass diffusion cell apparatus. The exposed area of the nasal membrane was approximately 0.64 cm². A test solution or suspension (3.5 ml) was introduced into the mucosal side of the membrane in the donor compartment while 3.5 ml of 10% ethanol, 40% propylene glycol, and 50% pH 7.4 isotonic phosphate buffer solution was added to the receptor compartment. The entire diffusion system was maintained at 37° C. throughout the experiment. At predetermined time intervals, 100 μl of the receptor solution was withdrawn for the assay and refilled with the same volume of fresh receptor medium to keep the volume constant. The steady-state flux value was determined from the slope of the straight line attained from the plot of the cumulative amount of drug permeated as a function of time. Each experiment was carried out in at least duplicate. This method was used in Examples 2–6.

A high pressure liquid chromatographic system equipped with a multi-solvent delivery system (Model 600E, Waters Associates, Milford, Mass.), an auto-injector (Model 717 Plus, Waters Ass.), a photodiode array detector (Model 996, Waters Ass.), a reverse phase Symmetric $C_{18}$ column (150 mm×3.9 mm ID, 5 μm), and a Millenium 2010 software computer system were used in this study. The mobile phases and UV wavelengths utilized for the analysis of diazepam, clonazepam, and (S)-2-carbamoyloxyl-1-o-chlorophenylethanol were 70% methanol, 30% water at 254 nm; 60% methanol, 40% water at 252 nm; 25% acetonitrile, and 75% water at 262 nm, respectively.

EXAMPLE 2

This example shows the effect of a bile salt and a lecithin dissolved in an aqueous medium at a 1% w/v level on the in vitro permeation of a model drug diazepam through the freshly excised nasal membrane. In these studies, a series of bile salts such as sodium cholate, sodium deoxycholate, sodium taurocholate, and sodium glycocholate, and a lecithin such as lysophosphtidylcholine were examined. The permeation rates were measured using the method described under the in vitro membrane permeation test method. The average steady-state transnasal flux data obtained in this manner are presented in Table I.

TABLE I

Effect of Bile Salts and Lecithin on the In Vitro Permeation of Diazepam across the Rabbit Nasal Mucosal Membrane at 37° C.

| Vehicle | Mean Transnasal Flux ($\mu g/cm^2/hr$) (n = 2) |
|---|---|
| Water | 79.5 |
| 1% Sodium Cholate/$H_2O$ | 66.3 |
| 1% Sodium Deoxycholate/$H_2O$ | 74.9 |
| 1% Sodium Taurocholate/$H_2O$ | 87.0 |
| 1% Sodium Glycocholate/$H_2O$ | 96.4 |
| 1% Lysophosphotidylcholine/$H_2O$ | 125.5 |

As seen from Table I, a bile salt such as sodium glycocholate and a lecithin such as lysophosphotidylcholine produce a significant enhancing effect on the diazepam permeation through the nasal membrane.

EXAMPLE 3

This example exhibits the influence of a vehicle on the in vitro membrane permeation of diazepam across the rabbit nasal mucous membrane at 37° C. In this experiment, a 1% diazepam suspension and solution were prepared using water and a co-solvent vehicle consisting of 30% ethanol (ETOH), 60% propylene glycol (PG), and 10% water (WT), respectively. The permeation rates were determined utilizing the method described in Example 1. The transnasal permeation profiles of diazepam obtained in this manner are presented in FIG. 1.

As seen from FIG. 1, a co-solvent vehicle comprising ethanol, propylene glycol, and water provides an approximately 8 times increase in the transnasal permeation rate of diazepam when compared with that obtained with an aqueous suspension.

EXAMPLE 4

This example shows the influence of the drug concentration in the donor compartment on the permeation of diazepam through the nasal mucous membrane, in vitro. In this study, 0.5–2% diazepam formulations were prepared using a co-solvent mixture comprising 30% ethanol, 60% propylene glycol, and 10% water. The in vitro membrane permeation rates were measured using the test method described in Example 1. The in vitro transnasal flux data obtained with diazepam formulations over 0.5–2% level is shown in FIG. 2.

Figure 2:
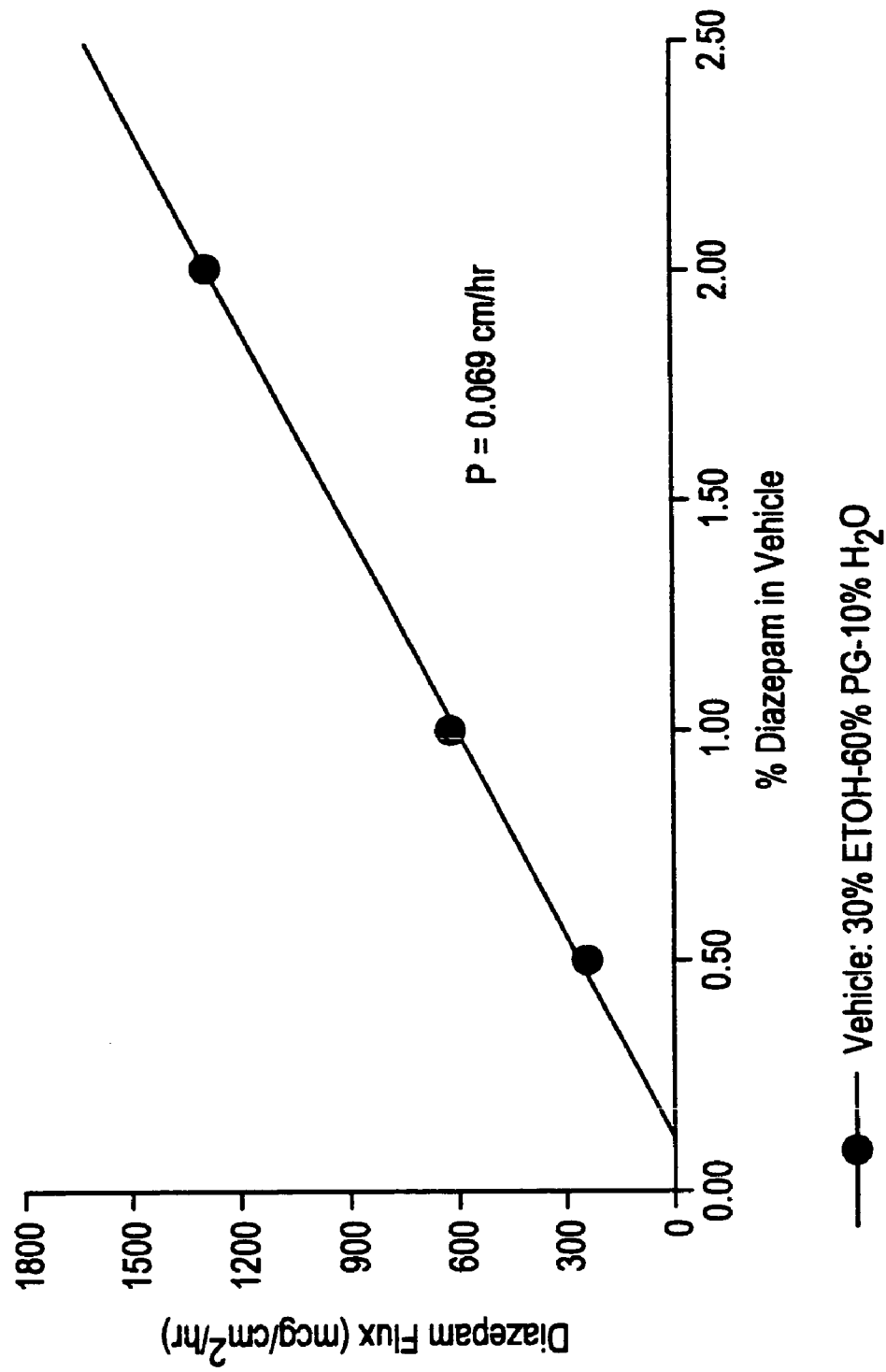
FIG. 2 is a graph showing the effect of drug concentration level on the in vitro transnasal permeation of diazepam from a vehicle of the invention.

As seen from FIG. 2, the steady-state transnasal flux of diazepam increases linearly with increasing the drug concentration in the donor compartment over the 0.5–2.0% concentration level.

EXAMPLE 5

This example shows the effect of the incorporation of a bile salt into a nasal formulation according to the invention on the in vitro transnasal membrane permeation of diazepam. In this experiment, the inclusion of sodium glycocholate to a vehicle consisting of 30% ethanol, 60% propylene glycol, and 10% water at a 1% level was examined. Sample drug solutions (10 mg/ml) were prepared with the vehicle with and without the bile salt. The membrane permeation rates were measured in the use of the test method described in Example 1. The in vitro permeation profiles obtained in this manner are presented in FIG. 3.

Figure 3:
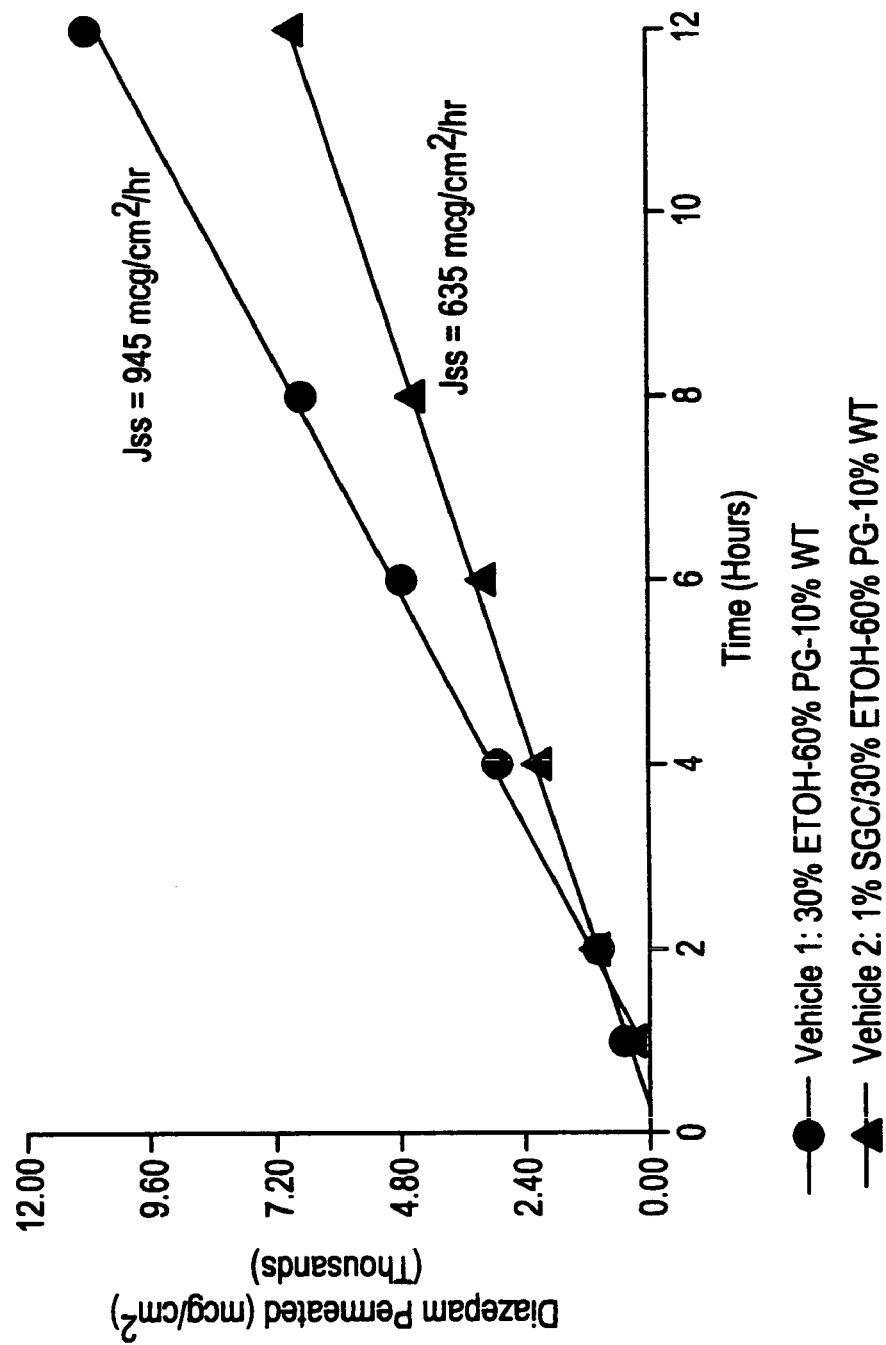
FIG. 3 is a graph showing the influence of sodium glycocholate (SGC) on the in vitro transnasal permeation of diazepam from a vehicle of the invention.

As seen from FIG. 3, the inclusion of a 1% level of sodium glycocholate enhances the transnasal permeation rate of diazepam significantly. An approximately 50% increase in the steady-state flux is noticed when the bile salt is incorporated into the vehicle.

EXAMPLE 6

This example shows the comparative transnasal permeabilities of three model drugs such as diazepam, clonazepam, and (S)-2-carbamoyloxyl-1-o-chlorophenylethanol. In this experiment, a co-solvent vehicle consisting of 30% ethanol, 60% propylene glycol, and 10% water was used. The in vitro permeation experiments were performed using the test method described in Example 1. The comparative transnasal permeability coefficient and steady-state flux data obtained with the medicaments at an initial drug concentration of 5 mg/ml are presented in Table II.

TABLE II

Comparative Transnasal Permeability of Model Drug Substances across the Rabbit Nasal Mucous Membrane In Vitro

| Drug Compound | Permeability Coefficient (cm/hr) | Transnasal Flux ($\mu g/cm^2/hr$) |
|---|---|---|
| Diazepam | $4.92 \times 10^{-2}$ | 246.0 |
| Clonazepam | $6.95 \times 10^{-2}$ | 347.7 |
| (S)-2-carbamoyloxyl-1-o-chlorophenylethanol | $9.77 \times 10^{-2}$ | 487.6 |

As seen from Table II, the monocarbamate based anticonvulsant, (S)-2-carbamoyloxyl-1-o-chlorophenylethanol appears to have approximately two times greater transnasal permeability as compared with that of diazepam.

EXAMPLE 7

Bioavailability and Pharmacokinetics of Diazepam Preparations

The bioavailability and pharmacokinetic characteristics of the preparations of the invention containing diazepam were tested after intranasal application to New Zealand White rabbits (n=3–4). For comparison, a diazepam injection (Formula 1 on Table III) was examined in vivo after intravenous administration of the same dose. IV Formula 1 (10 mg/2 ml) was obtained from Elkins-Sinn, Inc., which was prepared with propylene glycol (0.4 ml), alcohol (0.1 ml), benzyl alcohol (0.015 ml), sodium benzoate/benzoic acid (50 mg), and a sufficient quantity of water for injection to make 1 ml. For intranasal application, two formulations were prepared using a vehicle system of the invention consisting of 30% ethanol, 60% propylene glycol, and 10% water with (Formula 3 on Table III) and without (Formula 2 on Table III) 1% sodium glycocholate, respectively. Another nasal formulation (Formula 4 on Table III), prepared with a non-ionic surfactant vehicle of polyoxyethylated castor oil (Cremophor EL), was also tested after intranasal application for comparison since this formulation was tested in humans by Lau and Slattery (1989). All of the nasal formulations were prepared just prior to the experiments by dissolving 20-mg diazepam (Sigma Chemical) in 1 ml of the vehicles described above.

Figure 4:
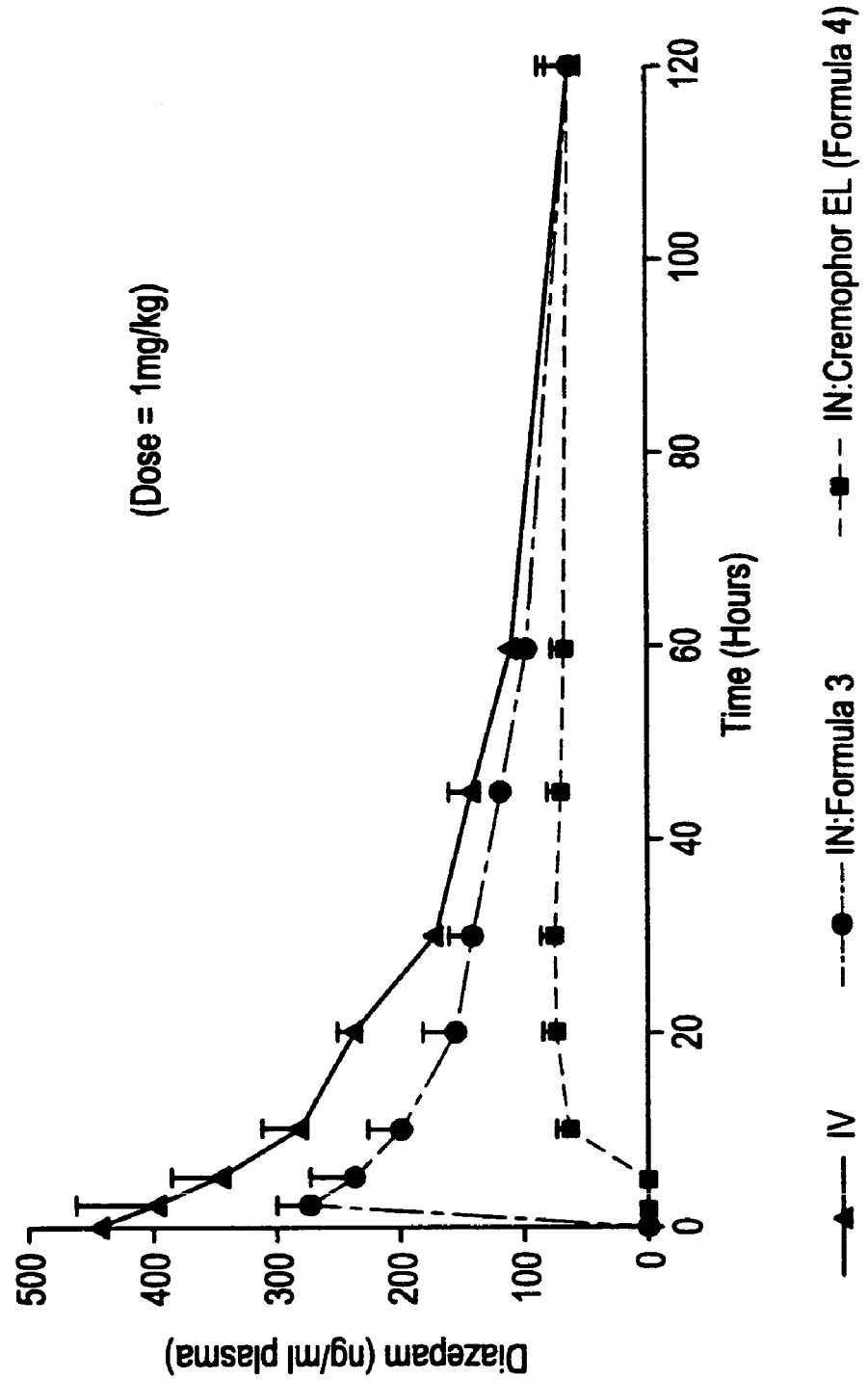
FIG. 4 is a graph showing the mean plasma concentration-time profiles of diazepam after intravenous (IV) administration and intranasal administration of a preparation in accordance with the invention (a single dose application).
Figure 5:
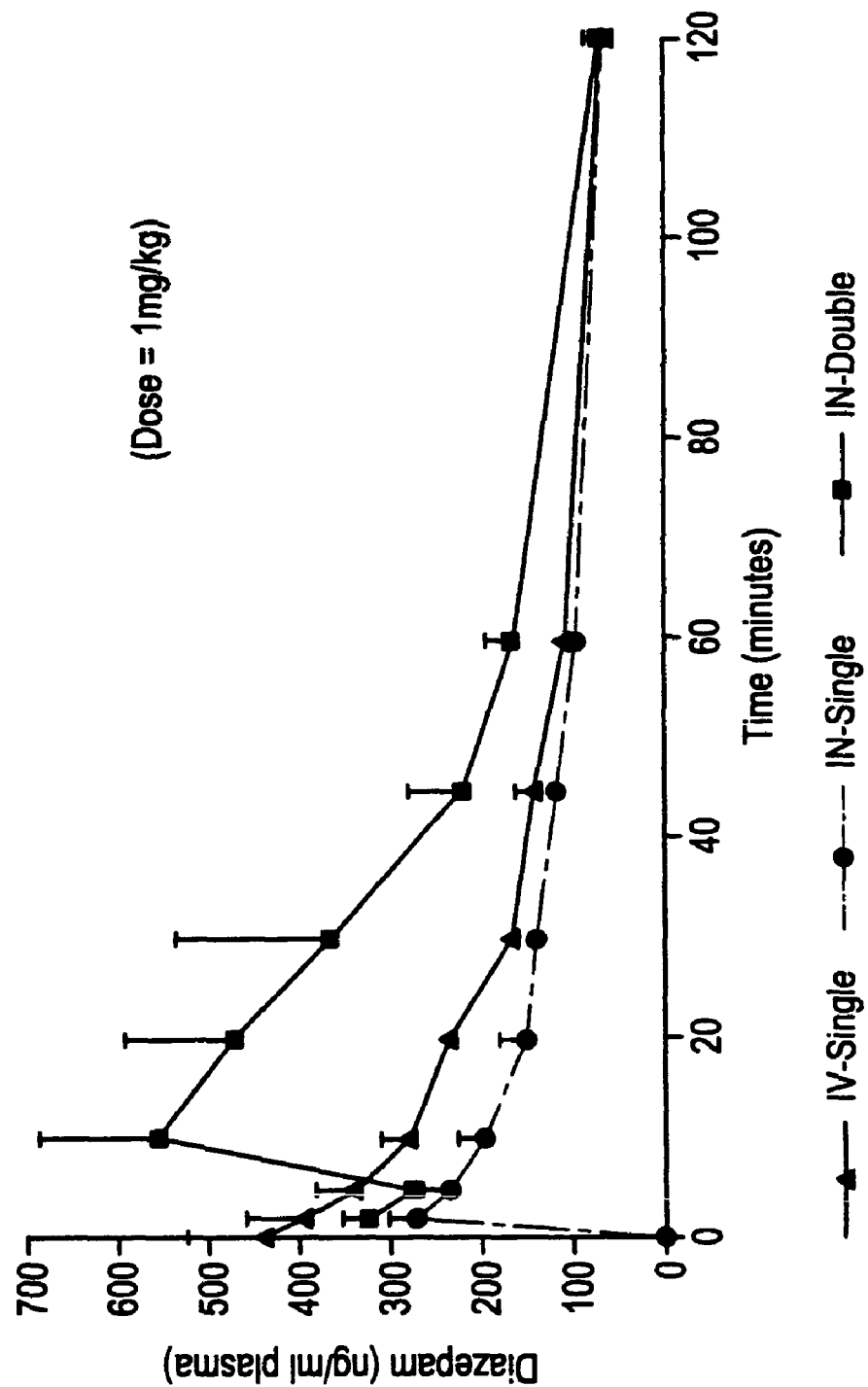
FIG. 5 is a graph showing the mean plasma concentration-time profiles of diazepam after intravenous and intranasal administration of a preparation in accordance with the invention (a multiple dose application).

Just prior to the experiment, rabbits (n=3–4) were weighed and restrained in rabbit restrainers while they were facing up. Each rabbit received 100 μl of the Formula 2 or 3 into each nostril by means of a Pfeiffer spray device within 5 seconds. Rabbits (n=3) having IV administration received 1 mg/kg of Formula 1 as an ear-vein infusing during 20 seconds. For the repeated dosing studies, the same volume of Formula 3 (100%1) was sprayed into each nostril 5 minutes after the first dosing. Blood samples (1 ml) were collected at 0, 2, 5, 10, 20, 30, 45, 60, and 120 minutes after the IV and IN administration. From the blood samples, plasma was separated by centrifugation and stored at −20° C. until analysis. For analysis, plasma samples (0.5 ml) were accurately transferred into a 1.5 ml polypropylene centrifuge tube. To the plasma sample, 0.5 ml of 0.01% v/v perchloric acid in an acetonitrile containing internal standard (clonazepam 1 μg/ml) was added. The mixture was vortexed for 30 seconds and centrifuged at 4000 rpm for 10 minutes. The plasma concentration of diazepam was assayed by HPLC. The analysis was performed with the Waters HPLC as described in Example 1. The column used in this study was a 3.9 mm×150 mm×5 μm Symmetric $C_{18}$ column. The mobile phase was 50% methanol: 10% acetonitrile: 40% pH 3.5 phosphate buffer by volume. The flow rate of the mobile phase was 1 ml/min and the UV detection was made at 228.5 nm. The detection limit for diazepam was 70 nmol/l. The areas (AUC) under the drug plasma concentration-time curves, from 0 min to 120 minutes, were calculated by means of the trapezoidal rule. The bioavailability and pharmacokinetic data obtained in this manner are listed in Table III. The comparative pharmacokinetic profiles obtained after a single IV administration (Formula 1) and a single and double IN applications of the preparations of the invention (Formulas 3 and 4) are depicted in FIGS. 4 and 5, respectively.

TABLE III

Bioavailability and Pharmacokinetic Parameter of Diazepam after IV and IN Administration of the Preparation of the Invention in Rabbits

| Route/Formulation | Dosing (mg/kg) | $C_{max}$ (ng/ml) | $T_{max}$ (min) | $AUC_{(0-120\ min)}$ (ng × min/ml) | F (%) |
|---|---|---|---|---|---|
| IV Formula 1[a] | Single (1 mg/kg × 1) | 398.8 (63.0)[d] | 2.0 | 17582 (407)[d] | 100.0 (n = 3) |
| IN Formula 2[b] | Single (1 mg/kg × 1) | 273.6 (62.2)[d] | 5.0 | 10383 (692)[d] | 59.1 (n = 3) |
| IN Formula 3[c] | Single (1 mg/kg × 1) | 273.7 (26.4)[d] | 2.0 | 13300 (972)[d] | 75.7 (n = 4) |
| IN Formula 3[c] | Double[f] (1 mg/kg × 2) | 327.1 (29.7)[d] 556.9 (130.5)[d] | 2.0 10.0 | 26787 (4859)[d] | 76.2[e] (n = 3) |
| IN Formula 4[g] | Single (1 mg/kg × 1) | 73.3 (11.9)[d] | 30.0 | 7497 (1445)[d] | 42.6 (n = 3) |

[a]IV Formula 1: 0.5% Diazepam Injection, USP, Elkins-Sinn, Inc., (PG/ETOH/Benzyl Alcohol/Sodium Benzoate/Benzoic Acid/Water for Injection)
[b]IN Formula 2: 2% Diazepam Solution in 60% PG, 30% ETOH, and 10% Water
[c]IN Formula 3: 2% Diazepam Solution in 1% SGC, 60% PG, 30% ETOH, and 10% Water
[d]Standard deviation
[e]Normalized data determined using the following equation: F = {$AUC_{IN,\ 1\ mg \times 2}/2 \times AUC_{IV,\ 1\ mg \times 1}$} × 100}
[f]Application time: $t_{zero}$: First dosing for nasal administration $t_{5\ minutes}$: Second dosing for nasal administration
[g]IN Formula 4: 2% Diazepam Solution in Cremophor EL As seen from FIG. 4 and Table III, IN Formula 3 prepared with 1% SGC, 30% ethanol, 60% PG, and 10% water increases the transnasal absorption markedly when compared with the Cremophor EL Formula 4. The $C_{max}$ and $AUC_{0-120\ minutes}$ for the IN Formula 3 are approximately 69% and 76% with reference to the IV administration, respectively. On the other hand, the $C_{max}$ and $AUC_{0-120\ minutes}$ for the Cremophor EL Formula 4 are about 19% and 42.6% of the IV injection. These comparative results appear to be consistent with the human pharmacokinetic data reported by Lau and Slattery (1989). According to the reported data, the Cremophor EL formulation yielded the $T_{max}$ of 1.4 hours after intranasal administration in humans and the $C_{max}$ was only about 27% relative to the IV injection. Surprisingly enough, as seen from FIG. 5 and Table III, a repeated intranasal application 5 minutes after the first dosing produces a marked increase in the transnasal absorption of diazepam. The $C_{max}$ and AUC values were exactly doubled after the second application relative to those obtained with the first administration. In addition, the plasma diazepam level attained after the second dosing exceeds that of the single IV administration within 7 minutes. These findings clearly demonstrate that a repeated dosing regimen (within a short period of time) can be effectively utilized for the acute management of epileptic seizures when a single intranasal dosing is incapable of producing the desired therapeutic effect.

EXAMPLE 8

Control of Peak Plasma Level Pharmacokinetics

Two mg of diazepam in a 100 μl vehicle was prepared and applied to rabbits (n=3) in a manner analogous to that described in Example 7. The following vehicles were tested: 60% ETOH, 30% PG, and 10% water (WT) with 1% SGC, 30% ETOH, 60% PG, and 10% water (WT) with 1% SGC, and 20% ETOH, 70% PG and 10% water (WT) with 1% SGC. Blood samples were collected from the ear vein at the following time intervals: 0, 2, 5, 10, 20, 30, 45, 60, and 120 minutes. The diazepam concentration in plasma was determined by HPLC. The pharmacokinetic profiles obtained after IV and IN administration of the preparations are presented in Table IV and FIG. 6.

TABLE IV

Effect of ETOH/PG Volume Ratio of the Vehicle on the Pharmacokinetic Parameter of Diazepam after IV and IN Administration of the Preparation of the Invention in Rabbits

| Route/Formulation | Dosing (mg/kg) | $C_{max}$ (ng/ml) | $T_{max}$ (min) | $AUC_{(0-120\ min)}$ (ng × min/ml) | F (%) |
|---|---|---|---|---|---|
| IV Formula 1[a] | Single (1 mg/kg × 1) | 398.8 (63.0)[e] | 2.0 | 17582 (407)[e] | 100.0 (n = 3) |
| IN Formula A[b] | Single (1 mg/kg × 1) | 313.2 (17.3)[e] | 2.0 | 13592 (692)[e] | 77.3 (n = 3) |
| IN Formula B[c] | Single (1 mg/kg × 1) | 273.7 (26.4)[e] | 2.0 | 13300 (972)[e] | 75.7 (n = 4) |
| IN Formula C[d] | Single (1 mg/kg × 1) | 246.3 (32.2)[e] | 2.0 | 12860 (827)[e] | 73.1 (n = 3) |

Figure 6:
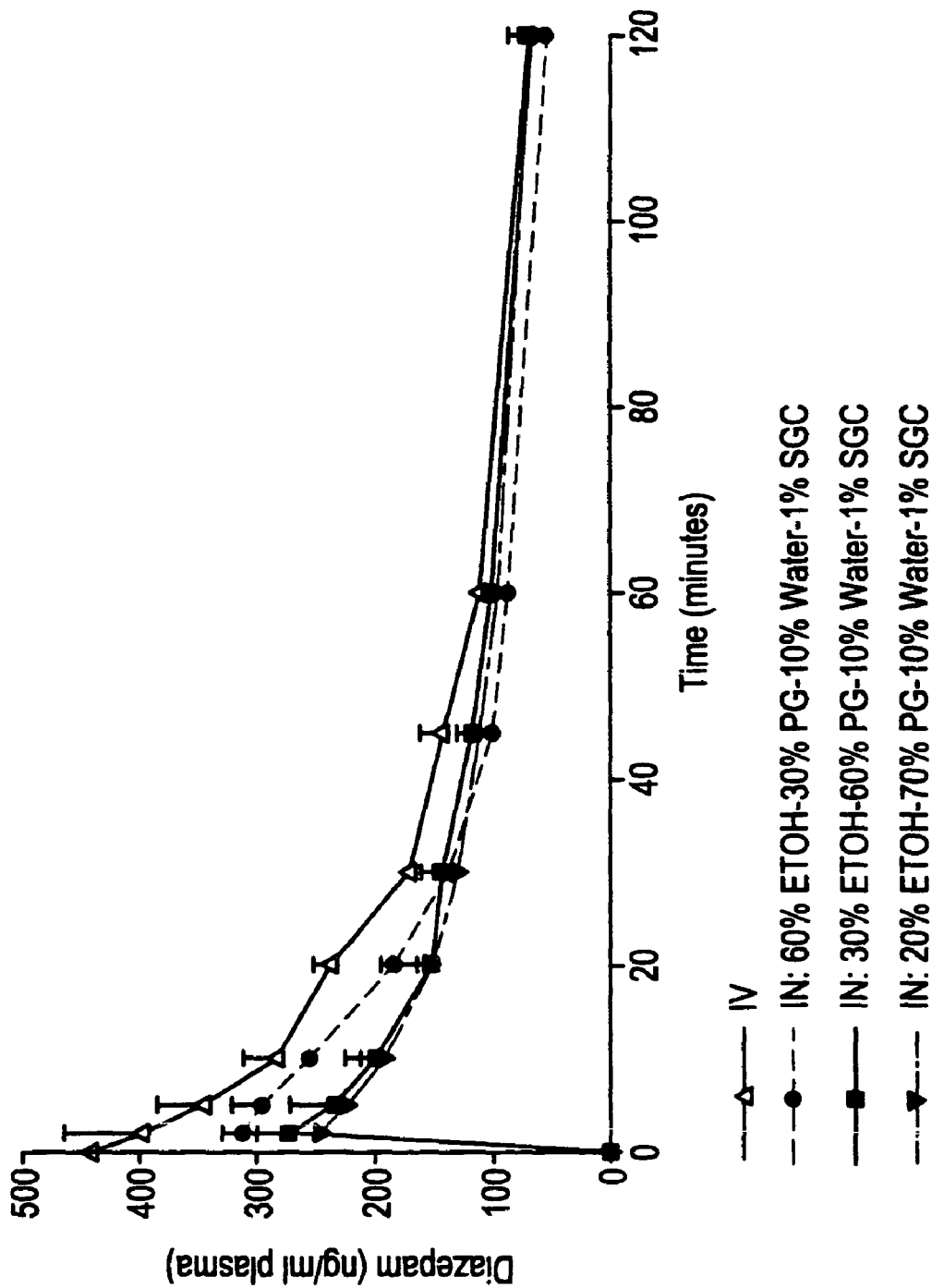
FIG. 6 is graph showing the mean plasma concentration-time profiles of diazepam after intranasal administration of a preparation as a function of propylene glycol/ethanol volume ratio in the preparation according to the invention.

[a]IV Formula 1: 0.5% Diazepam Injection, USP, Elkins-Sinn, Inc., (PG/ETOH/Benzyl Alcohol/Sodium Benzoate/Benzoic Acid/Water for Injection)
[b]IN Formula A: 2% Diazepam Solution in 1% SGC, 30% PG, 60% ETOH, and 10% Water
[c]IN Formula B: 2% Diazepam Solution in 1% SGC, 60% PG, 30% ETOH, and 10% Water
[d]IN Formula C: 2% Diazepam Solution in 1% SGC, 70% PG, 20% ETOH, and 10% Water
[e]Standard deviation As seen from Table IV and FIG. 6, the peak plasma concentration of the drug, observed within 2 minutes after the IN administration, can be controlled depending on the ETOH/PG volume ratio in the vehicles examined. The $C_{max}$ increases gradually with increasing the ETOH/PG volume ratio from 0.3 to 2. In addition, the peak plasma concentration for the IN vehicle consisting of 60% ETOH, 30% PG and 10% water (WT) with 1% SGC at 2 minutes is approximately 79% of an IV injection of the same dose.

In addition, modulating the ETOH/PG volume ratio in the vehicles can also control the plasma level-time profile in the elimination phase.

EXAMPLE 9

Pharmacological Response of Diazepam Preparations

The pharmacological response was examined in New Zealand White rabbits by evaluating muscle relaxation effect of diazepam after IV administration and IN administration of the preparations of the invention at a dosing level of 1 mg/kg. The vehicle of nasal formulation consisted of 30% ethanol, 60% propylene glycol, and 10% water containing 1% SGC. The sample formulation was prepared by dissolving 20 mg diazepam in 1 mL of the vehicle by ultrasonification. The IV formulation was the same as that used in Example 7. The pharmacological response was measured in rabbits after application of 100 μL of nasal formulation into each nostril while the rabbit was in a lying position after being firmly tipped with a finger on the hip. The mean response times that the rabbits remained in a lying position with its hind legs stretched to one side after IV and IN administration are listed in Table V.

TABLE V

Mean Pharmacological Response Times after IV and IN Administration of Diazepam Preparations

| Route/Formulation | Response Time (Min.) | N |
|---|---|---|
| IV Injection | 1.1 ± 0.2 | 3 |
| IN Formula 3 | 1.5 ± 0.5 | 3 |

As seen from Table V, the nasal formulation of the invention provides a very fast response. The time to pharmacological response was 1.5 minutes.

EXAMPLE 10

Bioavailability and Pharmacokinetics of Clonazepam Preparations

Figure 7:
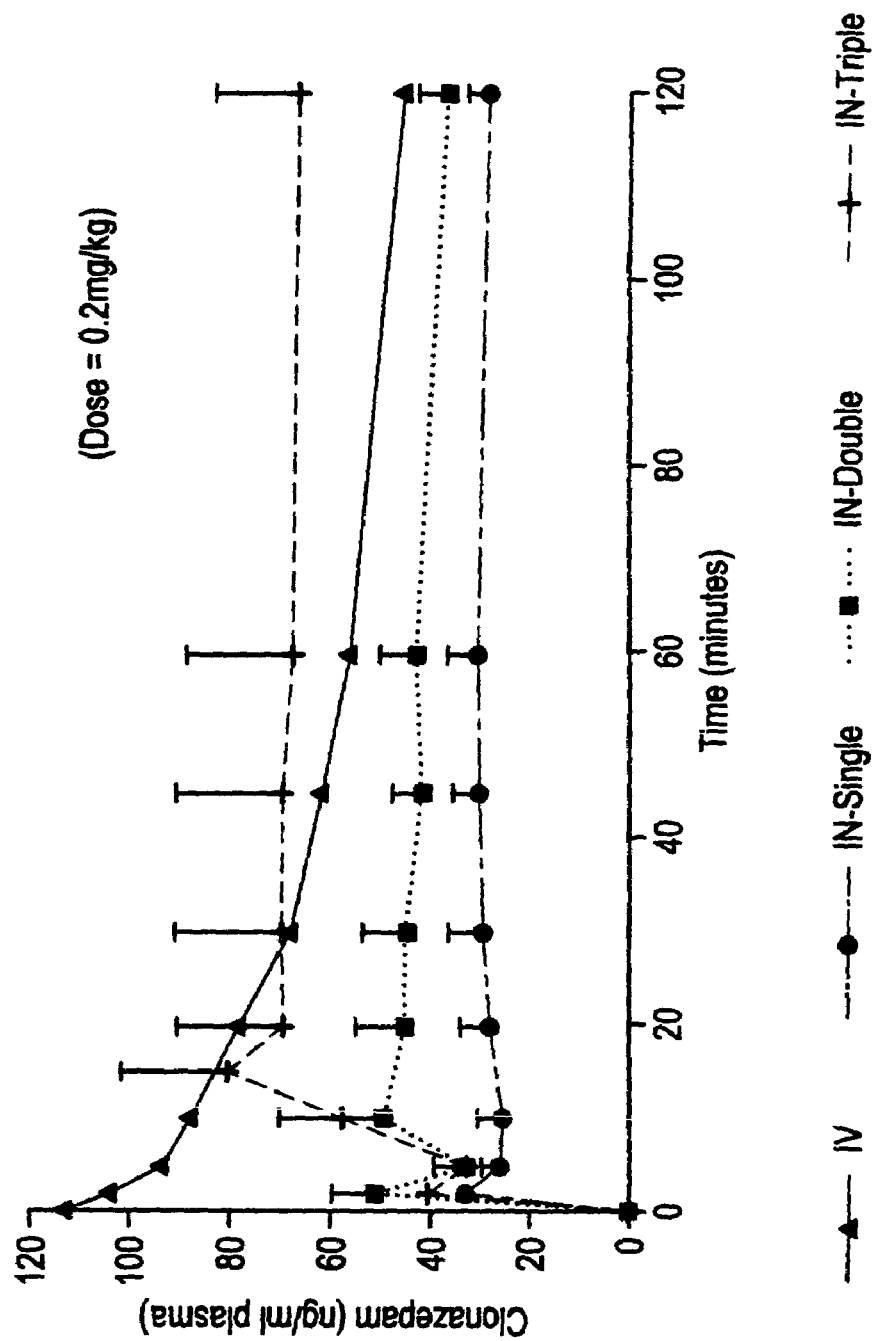
FIG. 7 is a graph showing the mean plasma concentration profiles of clonazepam after intravenous administration and intranasal administration of a preparation in accordance with the invention (a single and multiple dose application).

An intranasal formulation was prepared by dissolving 8.36 mg clonazepam in 2 ml of a vehicle of the invention consisting of 30% ETOH, 60% PG, and 10% water containing 1% SGC. A formulation for IV injection was prepared by dissolving 3-mg of clonazepam in 2 mL of a 40% PG, 30% ETOH, and 30% water solution and filtering the solution through a sterile filter under aseptic conditions. The formulations were administered to rabbits (n=3) at a dose of 0.2 mg/kg in a manner analogous to those described in Example 7. A repeated dosing regimen (double and triple application) at 5 minutes time intervals was also tested. Blood samples were obtained from the ear vein at the following time intervals: 0, 2, 5, 10, 20, 30, 45, 60, and 120 minutes. From the blood samples, plasma was separated by centrifugation and stored at −20° C. until analysis. For analysis, plasma samples (0.5 ml) were accurately transferred into a 15-ml test tube. To the plasma sample, 10 μl of an internal standard solution (diazepam—5 μg/ml) and 50 μl NaOH (0.5M) were added. To the above mixture, 5 ml of diethyl ether was added and this mixture was vortexed for 60 seconds and centrifuged at 4000 rpm for 10 minutes. The upper ethereal solution was transferred to a 5 ml test tube and evaporated in a vacuum evaporator at 40° C. for 30 minutes. The residue was reconstituted with 100 μl of the mobile phase for HPLC analysis consisting of 20% methanol, 30% acetonitrile, and a 50% pH 3.5 $KH_2PO_4/H_3PO_4$ buffer solution. The clonazepam concentration in the plasma was determined by HPLC using a flow rate of 1 ml/minute and the UV detection at 254 nm. The detection limit for clonazepam was 16 nmol/l. The bioavailability and pharmacokinetic data obtained after IV and IN administration in a single and multiple dosing schedule are listed in Table VI and the mean plasma concentration-time profiles are shown in FIG. 7.

TABLE VI

Bioavailability and Pharmacokinetic Parameters for Clonazepam after IV and IN Administration of the Preparations to Rabbits

| Route/Formulation | Dosing (mg/kg) | $C_{max}$ (ng/ml) | $T_{max}$ (min) | $AUC_{(0-120\ min)}$ (ng × min/ml) | F (%) |
|---|---|---|---|---|---|
| IV Formula[a] | Single (0.2 mg/kg × 1) | 104.8 | 2.0 | 7437.7 | 100.0 (n = 2) |
| IN Formula[b] | Single (0.2 mg/kg × 1) | 32.9 (5.9)[c] | 2.0 | 3356.4 (544.8)[c] | 45.1 (n = 3) |
| IN Formula[e] | Double[f] (0.2 mg/kg × 2) | 49.5 (5.3)[c] | 10.0 | 4896.8 (836.6)[c] | 32.9[d] (n = 3) |

TABLE VI-continued

Bioavailability and Pharmacokinetic Parameters for Clonazepam after IV and IN Administration of the Preparations to Rabbits

| Route/<br>Formu-<br>lation | Dosing<br>(mg/kg) | $C_{max}$<br>(ng/ml) | $T_{max}$<br>(min) | $AUC_{(0-120\ min)}$<br>(ng × min/ml) | F (%) |
|---|---|---|---|---|---|
| IN<br>Formula[d] | Triple[f]<br>(0.2 mg/kg × 3) | 80.2<br>(21.3)[c] | 15.0 | 7766.1<br>(2077.9)[c] | 34.8[e]<br>(n = 3) |

[a]IV Formula: 0.15% Clonazepam Solution in 40% PG, 30% ETPH and 30% Water
[b]IN Formula: 0.42% Clonazepam Solution in 1% SGC, 60% PG, 30% ETOH, and 10% Water
[c]Standard deviation
[d]Normalized data calculated using the following equation: F = {$AUC_{IN,\ 0.2\ mg\times2}/2 \times AUC_{IV,\ 0.2\ mg\times1}$} × 100
[e]Nomalized data calculated using the following equation: F = {$AUC_{IN,\ 0.2\ mg\times3}/3 \times AUC_{IV,\ 0.2\ mg\times1}$} × 100
[f]Application times: $t_{zero}$: First dosing for nasal administration $t_{5\ minutes}$: Second dosing for nasal administration $t_{10\ minutes}$: Third dosing for nasal administration As seen from Table VI and FIG. 7, the initial peak plasma concentration is attained within 2 minutes after the first intranasal application of the preparation. The peak plasma level was about 32% of the IV injection. However, after the third application at 5 minutes intervals, the peak plasma concentration observed at 15 minutes was nearly identical to that of the single IV injection of clonazepam.

EXAMPLE 11

Pharmacological Response of Clonazepam Preparations

The pharmacological response of clonazepam preparations was examined in New Zealand White rabbits after application of 100 µL of the 4.18 mg clonazepam/mL vehicle into each nostril in a manner analogous to that described in Example 9. The vehicle consisted of 30% ETOH, 60% PG, and 10% water containing 1% SGC. Clonazepam was dissolved in the vehicle by ultrasonification. The IV formulation used in the study was the same as described in Example 10. The mean response times measured after the W and IN administration are presented in Table VII.

TABLE VII

Mean Pharmacological Response Times after IV and IN Administration of Clonazepam Preparations

| Route/Formulation | Response Time (Minutes) | N |
|---|---|---|
| IV Injection | 1.7 ± 0.5 | 3 |
| IN Formulation | 1.4 ± 0.7 | 3 |

As shown in Table VII, the intranasal application of the clonazepam formulation of the invention provides a faster response time (1.4 minutes) when compared with that of IV injection (1.7 minutes).

EXAMPLE 12

Figure 8:
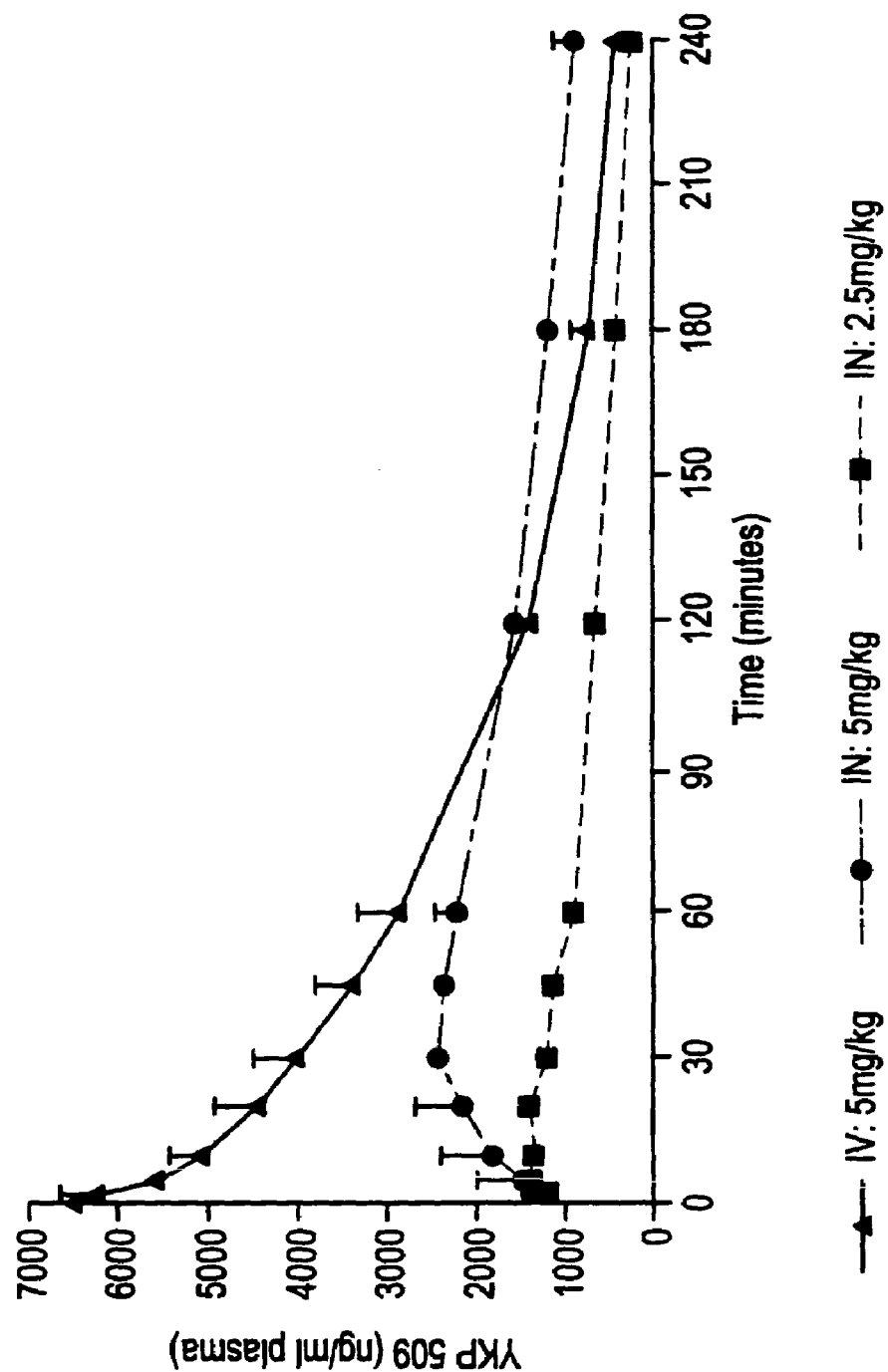
FIG. 8 is graph showing the mean plasma concentration-time profiles of (S)-2-carbamoyloxyl-1-o-chlorophenylethanol after intravenous administration and intranasal administration of a preparation according to the invention as a function of dose strength.
Figure 9:
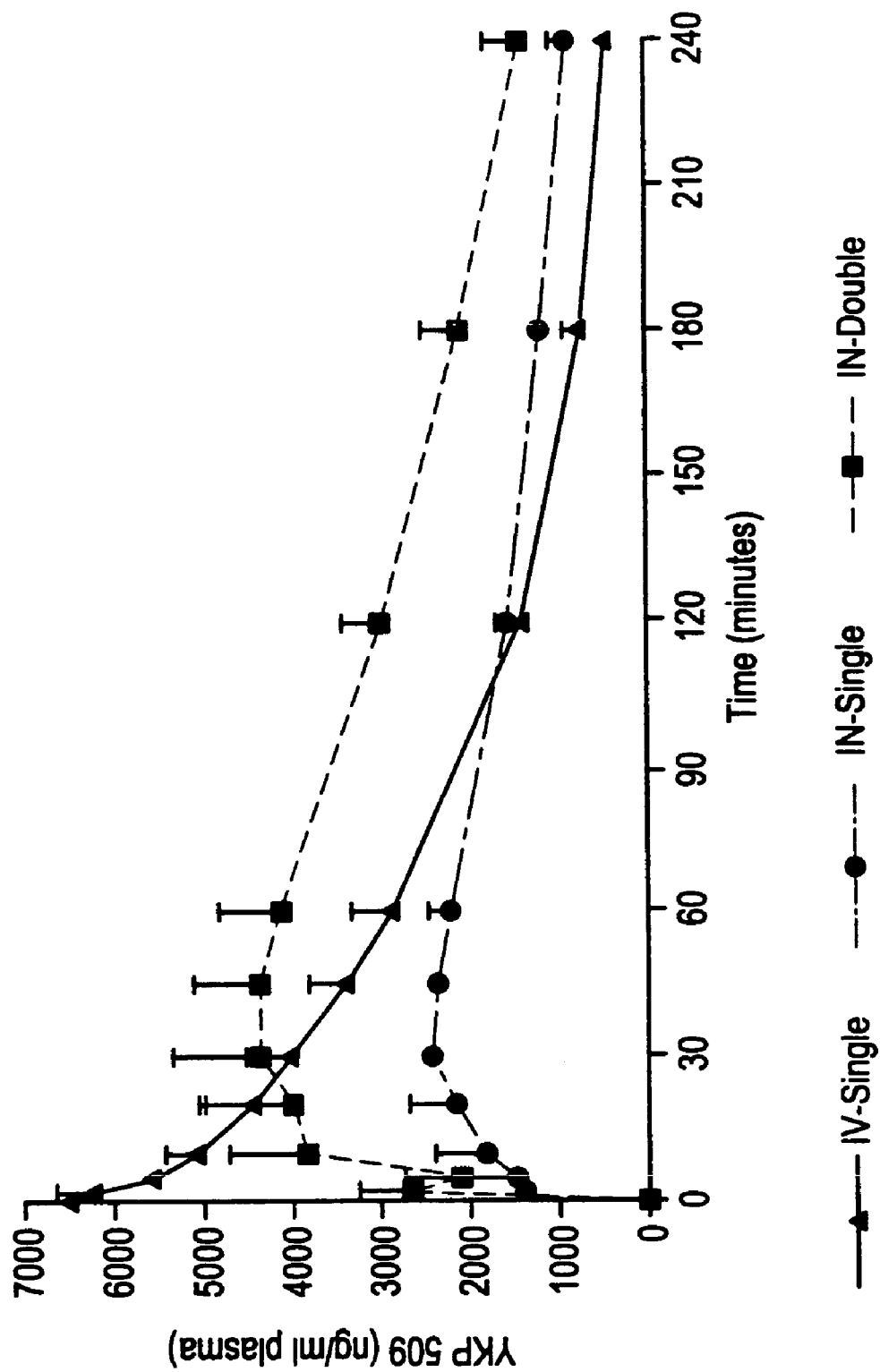
FIG. 9 is graph showing the mean plasma concentration-time profiles of (S)-2-carbamoyloxyl-1-o-chlorophenylethanol after intravenous administration and intranasal administration of a preparation according to the invention (a single and multiple dose application).

Bioavailability and Pharmacokinetics of (S)-2-carbamoyloxyl-1-o-chlorophenylethanol Preparations An intranasal formulation was prepared by dissolving 50 mg or 100 mg of a mono-carbamate based new anticonvulsive agent (S)-2-carbamoyloxyl-1-o-chlorophenylethanol in 1 mL of a vehicle of the invention consisting of 30% ETOH, 60% PG, and 10% water containing 1% SGC. A formulation for IV injection was prepared by dissolving 15 mg (S)-2-carbamoyloxyl-1-o-chlorophenylethanol in 1 mL of 40% PEG 400 and 60% water and filtering through a sterile membrane filter under aseptic conditions. The formulations were administered to rabbits (n=2–4) at the two dosing levels of 2.5 mg/kg and 5 mg/kg in a manner analogous to that described in Example 7. A repeated dosing regimen at 5 minute intervals was also studied in the nasal application of the preparation of the invention. Blood samples were obtained from the ear vein at the following time intervals: 0, 2, 5, 10, 20, 30, 45, 60, 120, 180 and 240 minutes. From the blood samples, plasma was separated by centrifugation and stored at −20° C. until analysis. For analysis, plasma samples (0.5 ml) were accurately transferred into a 15-ml test tube. To the plasma sample, 50 µl of an internal standard solution (2-(2,6-dichlorophenyl)-2-carbamoyloxyethyl)oxo-carboxamide–10 µg/ml) and 5 ml of methylbutyl ether were added. The mixture was vortexed for 60 seconds and centrifuged at 3500 rpm for 10 minutes. The upper ethereal solution was transferred to a 5 ml test tube and evaporated in a vacuum evaporator at 40° C. for 30 minutes. The residue was reconstituted with 200 µl of deionized water. The (S)-2-carbamoyloxyl-1-o-chlorophenylethanol concentration in the plasma was determined by HPLC in the use of a mobile phase consisting of 20% acetonitrile and 80% water with a flow rate of 1 ml/minute and UV detection at 210 nm. The detection limit for (S)-2-carbamoyloxyl-1-o-chlorophenylethanol was 23 nmol/l. The pharmacokinetic parameters determined after IV and IN administration of (S)-2-carbamoyloxyl-1-o-chlorophenylethanol at two dose strengths are presented in Table VIII. The bioavailability and pharmacokinetic parameters obtained after IV administration and IN administration of the preparations of the invention in a single and double dosing regimen are listed in Table IX. The mean plasma concentration-time profiles obtained after IV and IN administration of (S)-2-carbamoyloxyl-1-o-chlorophenylethanol preparations in single and double dosing schedules are presented in FIGS. 8 and 9.

TABLE VIII

Pharmacokinetic Parameters of (S)-2-carbamoyloxyl-1-o-chlorophenylethano after a Single IV and IN Administration at Two Dosing Strengths

| Route/<br>Formulation | Dose<br>(mg/kg) | Maximum<br>Conc.(ng/ml) | $T_{max}$<br>(min) | $AUC_{(0-240\ min)}$<br>(ng × min/ml) | F (%) |
|---|---|---|---|---|---|
| IV Formula[a] | 5.0 | 6267.7<br>(408.0)[d] | 2.0 | 473176<br>(56105)[d] | 100.0<br>(n = 4) |
| IN Formula 1[b] | 5.0 | 2404.9.<br>(130.0)[d] | 30.0 | 373991<br>(5077)[d] | 79.1<br>(n = 3) |
| IV Formula[a] | 2.5 | 4179.9 | 2.0 | 221291 | 100.0<br>(n = 2) |
| IN Formula 2[c] | 2.5 | 1407.2 | 5.0 | 160269 | 72.4<br>(n = 2) |

[a]IV Formula: 1.5% (S)-2-carbamoyloxyl-1-o-chlorophenylethanol solution in 40% PEG400 and 60% Water
[b]IN Formula 1: 10% (S)-2-carbamoyloxyl-1-o-chlorophenylethanol solution in 1% SGC, 60% PG, 30% ETOH and 10% Water
[c]IN Formula 2: 5% (S)-2-carbamoyloxyl-1-o-chlorophenylethanol solution in 1% SGC, 60% PG, 30% ETOH, and 10% Water
[d]Standard deviation

TABLE IX

Bioavailability and Pharmacokinetic Parameters of (S)-2-carbamoyloxyl-1-o-chlorophenylethano after IV and IN Administration of the Preparations in Single and Double Dosing Regimen

| Route/ Formulation | Dose (mg/kg) | Maximum Conc. (ng/ml) | $T_{max}$ (min) | $AUC_{(0–240\ min)}$ (ng × min/ml) | F (%) |
|---|---|---|---|---|---|
| IV Formula[a] | Single (5 mg/kg × 1) | 6267.7 (408.0)[c] | 2.0 | 473176 (56105)[c] | 100.0 (n = 4) |
| IN Formula[b] | Single (5 mg/kg × 1) | 2404.9. (130.0)[c] | 30.0 | 373991 (5077)[c] | 79.1 (n = 3) |
| IN Formula[b] | Double[e] (5 mg/kg × 2) | 4332.3 (979.3) | 30.0 | 700475 (114195)[c] | 74.0[d] (n = 3) |

[a]IV Formula: 1.5% (S)-2-carbamoyloxyl-1-o-chlorophenylethano solution in 40% PEG 400, and 60% Water
[b]IN Formula: 10% (S)-2-carbamoyloxyl-1-o-chlorophenylethano solution in 1% SGC 60% PG, 30% ETOH, and 10% Water
[c]Standard deviation
[d]Normalized data determined using the following equation: F = {$AUC_{IN,\ 5\ mg \times 2}$/2 × $AUC_{IV,\ 5\ mg \times 1}$} × 100}
[e]Application times: $t_{zero}$: First dosing for nasal administration $t_{5\ minutes}$: Second dosing for nasal administration As seen from Table IX, after the intranasal application the initial peak concentrations observed within 5–30 minutes increased proportionally with increasing the dose strength. The bioavailability of the nasal preparations is found to be 73–79% of the IV injection. The pharmacokinetic results presented in Table IX and FIG. 9 clearly demonstrate that the second application of the intranasal formulation 5 minutes after the first dosing produces a nearly identical bioavailability to that obtained after the first dosing. The $C_{max}$ and $AUC_{0-240\ minutes}$ are doubled after the second intranasal application. In addition, the plasma concentration of (S)-2-carbamoyloxyl-1-o-chlorophenylethanol achieved after the second dosing exceeded the plasma level obtained with a single IV injection at 30 minutes.

EXAMPLE 13

Stability Studies

In an effort to optimize the stability of the medicaments in the pharmaceutical compositions according to the present invention, an accelerated stability study was performed at a storage temperature of 37° C. over a 10–14 weeks time period. Sample drug solutions (0.1 mg/ml) were prepared using a vehicle of the invention consisting of 30% ETOH, 60% PG, and 10% water. The drug solutions were stored in an oven set at 37° C. At appropriate time intervals, a 100 μl sample was withdrawn and analyzed by means of HPLC. The chemical stability data determined in terms of the percent drug recovery are presented in Table X.

TABLE X

Chemical Stability of the Preparations of the Invention at 37° C.

| Drug Formulation | Storage Time (Weeks) | % Recovery |
|---|---|---|
| Diazepam Formulation | 0 | 100.0 |
|  | 4 | 100.3 |
|  | 10 | 102.4 |
|  | 14 | 102.6 |
| Clonazepam Formulation | 0 | 100.0 |
|  | 4 | 101.7 |
|  | 11 | 100.9 |
| (S)-2-carbamoyloxyl-1- | 0 | 100.0 |
| o-chlorophenylethanol Formulation | 3 | 100.2 |
|  | 4 | 98.2 |
|  | 9 | 98.0 |
|  | 12 | 97.6 |

What is claimed is:

1. A pharmaceutical composition for the administration of diazepam to the nasal mucosal membranes of a mammal in a rate-controlled manner of absorption comprising diazepam and an aqueous vehicle comprising: about 60% by volume of an aliphatic alcohol having from 1 to 5 carbon atoms; about 30% by volume of a glycol selected from the group consisting of propylene glycol, polyethylene glycol 200, polyethylene glycol 300, polyethylene glycol 400, and polyethylene glycol 600; about 1% by weight of a biological surfactant selected from the group consisting of a bile salt selected from the group consisting of sodium cholate, sodium deoxycholate, sodium glycocholate, sodium taurocholate, and sodium ursodeoxycholate and a lecithin selected from the group consisting of lysophosphotidylcholine, dipalmitoylphosphotidylcholin, distearoylphosphotidylcholin, dipalmitoylphosphotidylethanolamine, and dipalmitoylphosphotidylglycerol; and about 10% by volume of water.

2. A pharmaceutical composition for the administration of clonazepan to the nasal mucosal membranes of a mammal in a rate-controlled manner of absorption comprising clonazepam and an aqueous vehicle comprising: about 30% by volume of an aliphatic alcohol having from 1 to 5 carbon atoms; about 60% by volume of a glycol selected from the group consisting of propylene glycol, polyethylene glycol 200, polyethylene glycol 300, polyethylene glycol 400, and polyethylene glycol 600; about 1% by weight of a biological surfactant selected from the group consisting of a bile salt selected from the group consisting of sodium cholate, sodium deoxycholate, sodium glycocholate, sodium taurocholate, and sodium ursodeoxycholate and a lecithin selected from the group consisting of lysophosphotidylcholine, dipalmitoylphosphotidylcholin, distearoylphosphotidylcholin, dipalmitoylphosphotidylethanolamine, and dipalmitoylphosphotidylglycerol; and about 10% by volume of water.

3. A pharmaceutical composition for the administration of (S)-2-carbamoyloxy-1-o-chlorophenylethanol to the nasal mucosal membranes of a mammal in a rate-controlled manner of absorption comprising (S)-2-carbamoyloxy-1-o-chiorophenylethanol and an aqueous vehicle comprising: about 30% by volume of an aliphatic alcohol having from 1 to 5 carbon atoms; about 60% by volume of a glycol selected from the group consisting of propylene glycol, polyethylene glycol 200, polyethylene glycol 300, polyethylene glycol 400, and polyethylene glycol 600; about 1% by weight of a biological surfactant selected from the group consisting of a bile salt selected from the group consisting of sodium cholate, sodium deoxycholate, sodium glycocholate, sodium taurocholate, and sodium ursodeoxycholate and a lecithin selected from the group consisting of lysophosphotidylcholine, dipalmitoylphosphotidylcholin, distearoylphosphotidylcholin, dipalmitoylphosphotidylethanolamine, and dipalmitoylphosphotidylglycerol; and about 10% by volume of water.

* * * * *